(12) United States Patent
Buzot

(10) Patent No.: US 6,186,973 B1
(45) Date of Patent: Feb. 13, 2001

(54) TAMPON APPLICATOR

(75) Inventor: Herve Buzot, North Brunswick, NJ (US)

(73) Assignee: Johnson & Johnson GmbH (DE)

( * ) Notice: Under 35 U.S.C. 154(b), the term of this patent shall be extended for 0 days.

(21) Appl. No.: 09/331,907

(22) PCT Filed: Dec. 23, 1998

(86) PCT No.: PCT/EP98/08400

§ 371 Date: Sep. 8, 1999

§ 102(e) Date: Sep. 8, 1999

(87) PCT Pub. No.: WO99/33429

PCT Pub. Date: Jul. 8, 1999

(30) Foreign Application Priority Data

Dec. 24, 1997 (DE) .............................................. 197 58 376

(51) Int. Cl.[7] .......................... A61F 13/20; A61M 31/00; A61M 35/00
(52) U.S. Cl. ................................ 604/17; 604/15; 604/60; 604/286; 604/311
(58) Field of Search ........................... 604/11–18, 57–60, 604/64, 218, 311, 285–288, 904

(56) References Cited

U.S. PATENT DOCUMENTS

| | | | |
|---|---|---|---|
| 2,355,917 | * 8/1944 | Knight | 604/15 |
| 2,416,642 | * 2/1947 | Popper | 604/15 |
| 2,647,512 | * 8/1953 | Johnson | 604/64 |
| 3,831,605 | * 8/1974 | Fournier | 604/285 |
| 4,269,187 | * 5/1981 | Sakurai et al. | 604/16 |
| 4,273,125 | * 6/1981 | Sakurai | 604/16 |
| 4,329,991 | * 5/1982 | Sakurai | 604/16 |

FOREIGN PATENT DOCUMENTS

532745 * 1/1941 (GB) ..................... 604/15

* cited by examiner

*Primary Examiner*—Dennis Ruhl

(57) ABSTRACT

The invention relates to a tampon applicator. The tampon applicator is intended to permit easier and safer handling of the tampon. For this purpose, the tampon comprises a hollow outer cylinder (10) with a delivery opening (12) for allowing to push out the tampon (2) which outer cylinder has an opening (14) in the cylinder wall which is located behind the rearward end (3) of the tampon (2) when the tampon (2) is in its initial position in the hollow outer cylinder (10) with its forward end adjacent the delivery opening (12). In addition, an elongated pusher element (20) is provided adapted to be insertable in and slidable through the opening (14) into the interior of the outer cylinder (10) in order to abut with its forward end portion against the rearward end (3) of the tampon (2). Further, the tampon applicator comprises a push lever (30) being pivotally connected to a rearward end portion (32) of the elongated pusher element (2) and being pivotally connected to the outer cylinder in a position behind the opening (14) such that by pivoting the push lever (30) forward towards the outer cylinder the elongated pusher element (20) is advanced through the opening (14) to thereby push out the tampon (2) through the delivery opening (12).

13 Claims, 2 Drawing Sheets

TAMPON APPLICATOR

The invention relates to an applicator type tampon having an outer cylinder which contains the tampon. The tampon can be pushed out through a forward delivery opening of the outer cylinder.

BACKGROUND OF THE INVENTION

A simple applicator of the prior art comprises an outer cylinder which holds in its interior a tampon near its forward end portion. An inner cylinder or plunger is inserted through a rearward opening of the outer cylinder and is slideable therein. When sliding the inner cylinder forward its front end abuts against the rearward end of the tampon, whereby the tampon, upon further advancing the inner cylinder, is pushed through the delivery opening out of the outer cylinder. An applicator of this type has a length of about 2.5 times the length of the tampon.

DE 30 11 612 (corresponding to U.S. Pat. No. 4,373,125) discloses a tampon applicator comprising an outer cylinder and a pusher cylinder. The pusher cylinder is cut open in its front portion such that two elongated bars or legs are formed which, in cross section perpendicular to the longitudinal axis of the pusher cylinder, have the shape of segments of the original cylinder wall. In its rearward portion the outer cylinder is provided with openings which are located behind the rearward end of the tampon when the latter is in its initial position in the outer cylinder. The openings are dimensioned so that through each opening one of the bars or legs of the pusher cylinder can be slid into the interior of the outer cylinder. Before use the pusher cylinder is positioned with its elongated bars engaging the outer wall of the outer cylinder and with its cylindrical end portion being located behind the rearward end of the outer cylinder. To use the applicator the pusher cylinder is first pulled back until the front ends of said elongated bars are in registration with the openings in the outer cylinder. Then, the forwards ends of the bars are introcuded into the openings and slid into the interior of the outer cylinder by pushing the pusher cylinder forward. In order to facilitate introduction of the elongated bars into the openings, the latter can be oriented in an inclination against the longitudinal axis of the cylinder, i.e. they can be located in a tapered portion of the outer cylinder, so that the bars can easily be introduced by moving their forward end portions through the openings into the interior of the outer cylinder. If the pusher cylinder is then pushed forward further, the elongated bars slide forward in the interior of the outer cylinder until they abut against the rearward end of the tampon located in the forward end portion of the outer cylinder. By further advancing the pusher cylinder the tampon is then pushed through the delivery opening out of the outer cylinder. The elongated bars have a certain flexibility or capability to bend along their longitudinal direction so that before use of the applicator they can lie on the outer surface of the outer cylinder and can, after introduction of the tips into the openings, move forward in abutment against the inner wall of the outer cylinder. A similar tampon applicator having a pusher cylinder with elongated bars which can be introduced through openings in the outer cylinder wall into the interior of the outer cylinder and are slideably moveable therein to push a tampon out of the delivery end of the outer cylinder is described in DE 30 31 838 (corresponds to U.S. Pat. No. 4,329,991).

One disadvantage of these known applicators is that the outer cylinder and the pusher cylinder can be disengaged. Consequently the outer cylinder and the pusher cylinder can easily fall apart if they are not in close frictional engagement with each other. If, on the other hand, there is considerable friction between the outer cylinder and the pusher cylinder which, as mentioned, is needed so that both parts do not easily fall apart, it is very difficult to move the pusher cylinder against the strong friction relative to the outer cylinder. For this reason, comparatively strong forces are needed to push the tampon out of the outer cylinder. These frictional forces even increase with further advancing the pusher cylinder since the contact area on the inner wall of the cylinder increases. While moving the pusher cylinder against the friction forward it can also happen that it gets stuck within the outer cylinder.

Problems with frictional forces between the puhser cylinder and the outer cylinder in particular arise when environmental conditions like temperature, humidity etc. change which can result in a substantial increase of the force needed to press the pusher cylinder forward into the outer cylinder to push out the tampon.

It is an object of the present invention to provide a tampon applicator which can easily be handled and which allows to push out the tampon in an easy and safe way.

SUMMARY OF THE INVENTION

According to the present invention the outer cylinder for holding the tampon is provided with an opening in its cylinder wall, which opening is located behind the rearward end of the tampon when the tampon is in its initial position in the outer cylinder, with the front end of the tampon being adjacent the delivery opening. An elongated pusher element can be introduced through the opening into the interior of the outer cylinder so that a forward end portion of the elongated pusher element, after sliding the pusher element forward through the opening, abuts against the rearward end of the tampon. The rearward end portion of the elongated pusher element in turn is pivotally connected to a push lever. The push lever is pivotally connected to the outer cylinder, wherein the latter pivotal connection is located behind the opening in the wall of the outer cylinder. Thus, the push lever forms a lever which, when turned forward relative to the outer cylinder, advances the pusher element connected to it. After the leading end of the pusher element has been introduced into the opening, turning the push lever further results in advancing the pusher element in the interior of the cylinder and eventually in pushing out the tampon.

With the arrangement of the tampon applicator according to the invention the tampon can be released from the outer cylinder of the applicator in a particularly simple and safe way. Before use of the applicator, the push lever and the elongated pusher element can lie on the exterior surface of the outer cylinder. For using the applicatior the push lever is then pivoted away from the outer cylinder and the forward end of the pusher element is inserted into the opening in the cylinder wall and pushed forward until it abuts against the rearward end of the tampon within the outer cylinder. Then, the push lever is pivoted further toward the outer cylinder, whereby the elongated pusher element is moved forward through the opening and is further advanced in the interior of the outer cylinder, thereby pushing the tampon forward and finally through the delivery opening out of the outer cylinder.

Since the pusher elements extends from a position in the exterior and spaced apart from the outer cylinder to a position within the outer cylinder, and extends in the interior of the outer cylinder essentially coaxially to the longitudinal axis of the cylinder, it has to have a certain bending capability along its longitudinal axis so that it can follow a slightly bent path. In one embodiment the pusher element can simply be an elongated rod made of plastic or cardboard, the diameter of the rod being chosen so that the pusher rod has the desired bending flexibility. The push lever can, for example, have the form of a flat bar and can be more rigid than the pusher element. The thickness can for example be three times the thickness or diameter of the pusher element rod. A higher rigidity of the push lever makes it easier for the user to exert force on the push lever while turning it, and to transfer the force effectively to the pusher element to move it forward.

The applicator according to the invention is advantageous since it eliminates any substantial frictional forces between the outer cylinder and the pusher element, thus allowing that the pusher element can be easily and smoothly advanced. Thus, problems of substantial forces needed to slide the pusher element forward or problems with pushers stuck in the outer cylinder are completely eliminated.

The applicator of the invention is further advantageous in utilizing a lever, namely the push lever, to cause the forward movement of the pusher element. In this manner, by using the turning movement of the push lever which is transmitted to the pusher element and further to the tampon, the tampon can be pushed out in a very controlled and comfortable way since the user can turn the push lever by pressing with her thumb on it while gripping the outer cylinder between two fingers. Furthermore, with the push lever a torque is exerted which can, if the push lever extends beyond its connection to the pusher element, facilitate use of the applicator since less force is needed to push out the tampon.

The applicator of the invention is furthermore advantageous since its parts are permanently connected to each other so that no part can inadvertently be removed or be lost.

In a particulary preferred embodiment the outer cylinder, the push lever and the pusher element are integrally formed as a single piece, for example as an injection moulded plastic part. The pivotal connections between outer cylinder and push lever and between push lever and pusher element can be formed of zones of weakened material thickness which allow the connections to be folded around their weakened bridges or joints.

It is a further advantage of the invention that the outer cylinder can be rather short in longitudinal direction, i.e. the ratio of the overall length of the applicator to the tampon can be as small as 2:1.

In the applicator according to the invention the outer cylinder, the push lever and the pusher element can be made of plastic, biodegradable material or cardboard. In particular plastic materials such as polyethylene, polypropulene, polyurethane, polyesters, ethylene-vinyl acetate, polystyrene can be used to form the applicator of the invention. Biodegradable materials which can be used to form the applicator of the invention are for example described in EP 0 606 923 A1; suitable biodegradable materials are for example poly(vinyl alcohol), polyoxyethylene, and the like.

In a preferred embodiment the outer cylinder is provided with a cut-out at its rearward end, leaving a slot in the wall which can be located for example opposite to the connection of the push lever. This slot in the rearward end of the outer cylinder wall is dimensioned to receive the string of the tampon. This allows the string of the tampon which would otherwise be loosely hanging out of the rearward opening of the outer cylinder to be lead through the slot and thus out of the way so that it cannot be caught between the finger of the user and the rearward end of the outer cylinder or in any other way interfere when the user is handling the applicator for insertion of the tampon. The width of the slot is preferably slightly lower than the diameter of the string so that the string when inserted through the slot is held therein.

In a further preferred embodiment the push lever is provided with a hook which is arranged to be insertible through the opening in the outer cylinder wall when the push lever is folded against the outer cylinder wall. This hook which is preferably made of elastic material and preferably integrally formed with the push lever is arranged to be releasably snapped into the opening of the outer cylinder wall and thus permits the push lever to be safely held against the outer cylinder for transport and tampon loading.

The invention is further described hereinafter in connection with preferred embodiments illustrated in the drawings, in which:

DETAILED DESCRIPTION OF THE INVENTION

Figure 1:
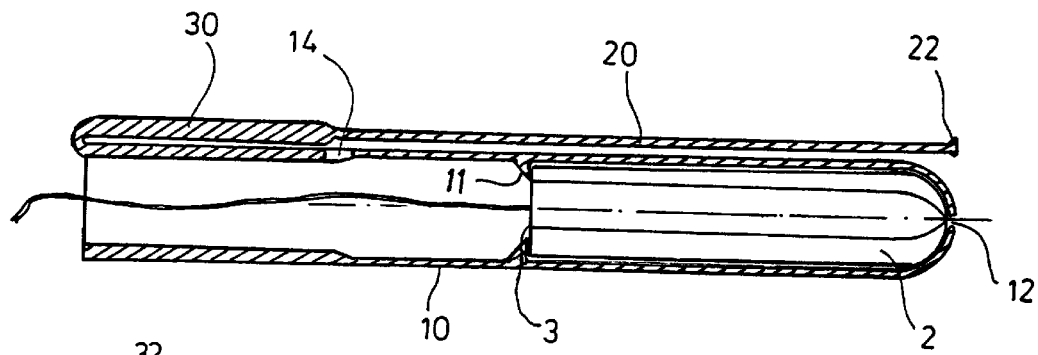
FIG. 1 shows a schematical cross sectional view of a first embodiment of the tampon applicator in its initial position before use.

FIG. 1 shows the tampon applicator in its initial position, before use, as it is removed by the customer from its package. The tampon applicator comprises an outer cylinder 10 having a cylindrical hollow interior into which a tampon 2 is inserted. The outer cylinder 10 can have a uniform wall thickness; it is, however, preferred that, as illustrated, the wall thickness is increased in a rearward end portion. This end portion with increased wall thickness can for example extend from an opening 14 to the rearward end of the outer cylinder 10. The increased wall thickness provides more structural strength or rigidity in the rearward end portion where the user grips the applicator and exerts forces when pushing out the tampon 2. The ratio of the increased wall thickness to the wall thickness in the forward portion of the outer cylinder should be in the range from 4:1 to 1:1, preferably between 3:1 and 2:1.

The tampon 2 is positioned within the interior of the outer cylinder 10 so that the front end portion of the tampon 2 is located adjacent to a delivery opening 12 at the front end of the outer cylinder 10. Stops 11 on the inner wall of the outer cylinder 10 prevent the tampon froming moving backward from its position adjacent to a delivery opening 12. In the illustrated embodiment the stops 11 have, in the section shown in FIGS. 1–3, a wedge-like shape, with a sloping portion which allows to slide the tampon past the stops when introducing it into the outer cylinder, and with a vertical portion which prevents the tampon from moving backward again once it is in the desired position with its forward end at the delivery opening 12.

The outer cylinder 10 is further provided with a push lever 30 which is with one of its ends 34 pivotally connected to the exterior of the outer cylinder 10. At its other end 32 the push lever 30 is pivotally connected to an elongated pusher element 20. An opening 14 is provided in the outer wall of the outer cylinder 10. Through this opening 14 the elongated pusher element 20 can be, with its front end portion 22 leading, slid into the interior of the outer cylinder 10. The opening 14 is located in longitudinal direction between the rear end 3 of the tampon 2 and the rear end 34 of the push lever 30 which is pivotally connected to the outer cylinder 10. More preferably the opening 14 is located in longitudinal direction between the rear end 3 of the tampon 2 and the forward end 32 of the push lever 30, in particular the opening 14 can be, as in the illustrated embodiments, located at the position of the forward end 32 of the push lever 30 when the latter is folded against the outer cylinder 10 as shown in FIG. 1.

In a preferred embodiment the outer cylinder 10, the push lever 30 and the pusher element 20 are integrally formed as a single piece, wherein the pivotal connections between the outer cylinder 10 and the push lever 30 at its end 34 and between the pusher element 20 and the push lever at its end 32 are realized by zones of weakened material thickness. The push lever 30 is, as illustrated, preferably thicker than the pusher element 20 in order to have more rigidity so that the user can safely press on it and the force is transmitted to the pusher element 20 essentially without bending of the push lever 30.

In order to use the tampon applicator of FIG. 1 which is shown in its initial or start position, the push lever 30 is pivoted away from the outer surface of the outer cylinder 10, and the tip 22 of the pusher element 20 is inserted into the opening 14 in the cylinder wall. For this purpose the position of the opening 14 on the outer cylinder 10 as well as the lengths of the push lever 30 and the pusher element 20 have to be adjusted to each other so that the front end portion 22 of the pusher element 20 can be brought into a position over the opening 14. As in the illustrated embodiment this is for example achieved if the length of the push lever 30 is about half of the length of the pusher element 20 and if the opening 14 is located at a distance spaced apart from the pivotal joint of the push lever 30 by a distance corresponding to the length of the latter. In this case, by completely folding the push lever 30 from the initial position shown in FIG. 1 by about 180°, the front end portion 22 of the pusher element 20 comes into the area of the opening 14. However, for the dimensions and relative positions many variations and modifications from the described relative dimensions of the parts are possible. For example, the opening 14 could also be spaced apart from the pivotal connection of the push lever 30 by a distance larger than the length of the latter so that it does not have to be folded back completely in order to bring the front end portion 22 to the area of the opening 14. In case of modified dimensions and relative positions the bending capability of the pusher elemeent 20 can also be utilized in order to allow to insert a front end portion into the opening 14.

Figure 4:
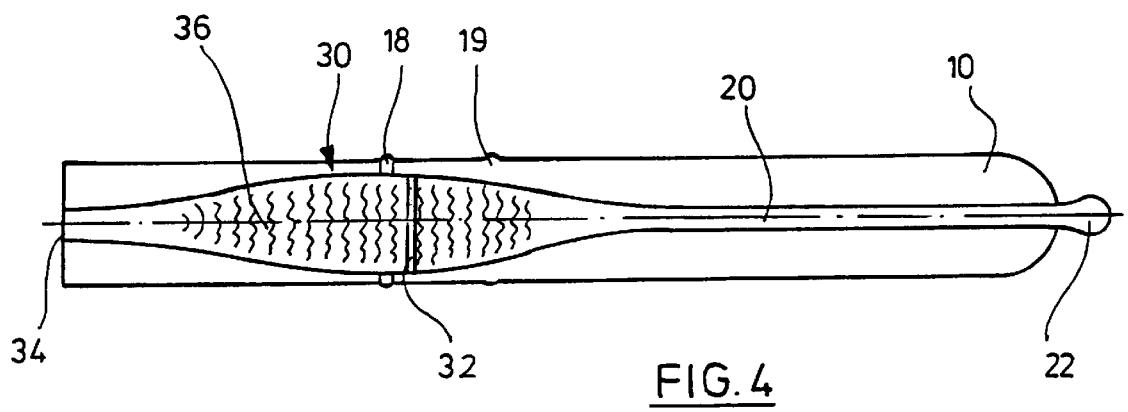
FIG. 4 shows a top view of the preferred embodiement of the applicator.
Figure 5:
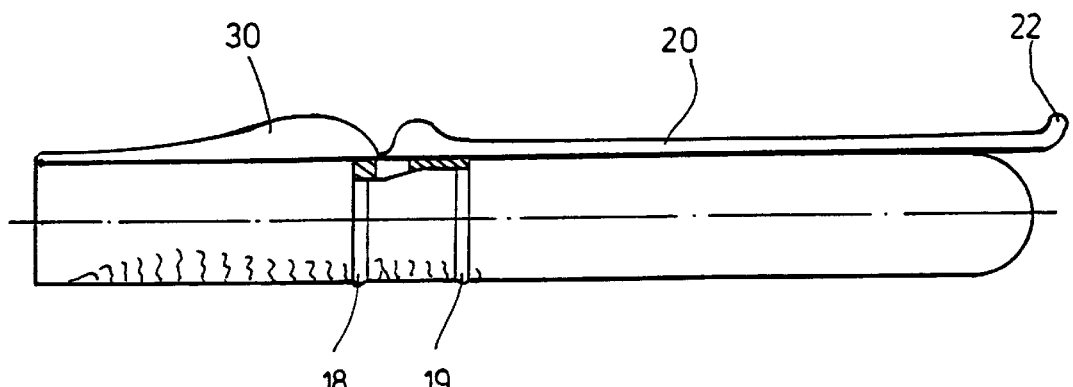
FIG. 5 shows a side view of the applicator of FIG. 4.

In FIG. 4 a top view of another applicator is shown. In this embodiment the push lever 30 has a broadened portion to present a support surface 36 against which the thumb of the user can press for turning the push lever 30. The support surface 36 is provided with a non-planar profile so that the thumb has a good grip and cannot easily slide against the support surface 36. Furthermore, the outer cylinder is provided with two circumferential rings or flanges 18, 19 which allow the user to hold the outer cylinder between two fingers, without any danger of the cylinder sliding in longitudinal direction.

Figure 2:
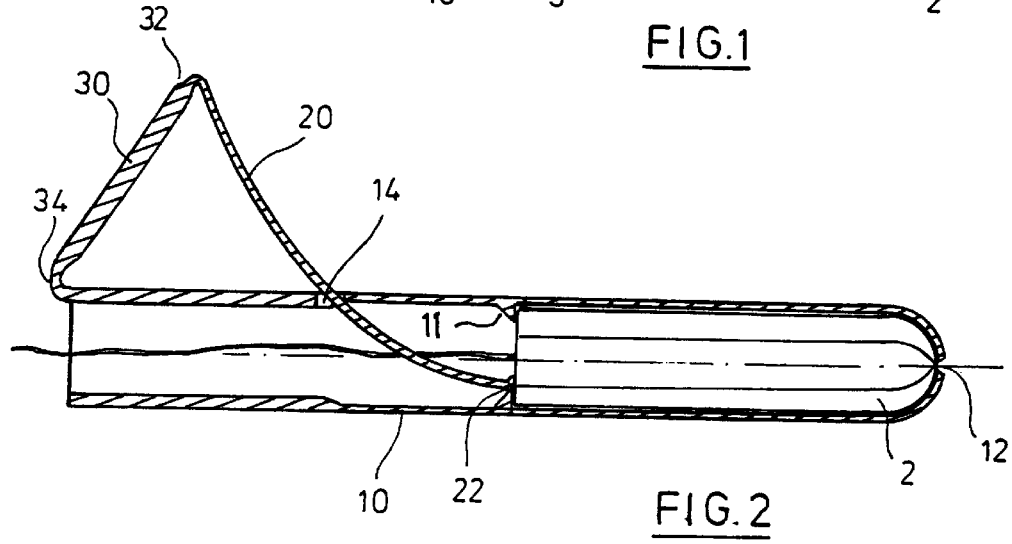
FIG. 2 shows the tampon applicator of FIG. 1 in a position immediately before pushing the tampon out.
Figure 3:
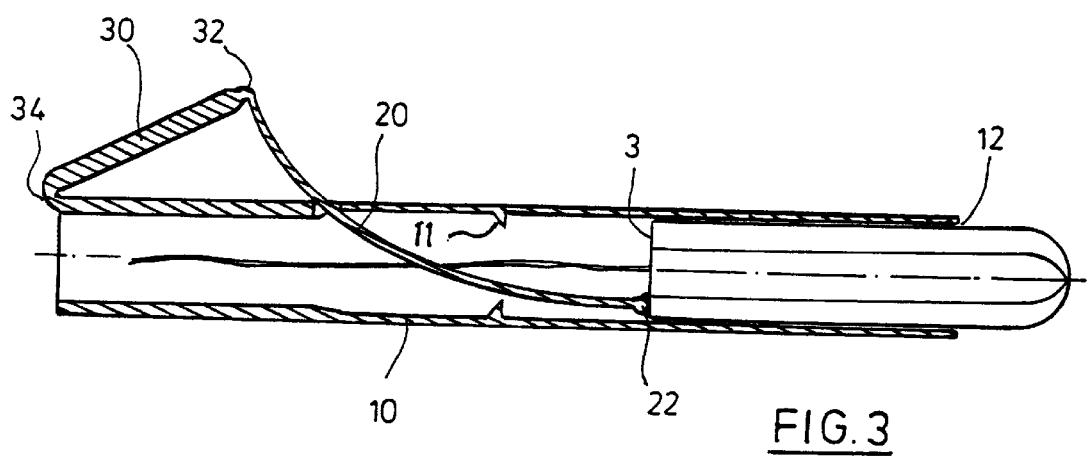
FIG. 3 shows the tampon applicator of FIGS. 1 and 2 in an intermediate position in which the tampon is already half way pushed out.

In order to use the applicator shown in FIG. 1, the push lever 30 is folded back and the front end portion 22 of the pusher element 20 is inserted through the opening 14 into the interior of the outer cylinder 10. Then, by further turning the push lever 30 towards the outer surface of the outer cylinder the pusher element 20 is being slid further into the interior of the outer cylinder 10 and eventually contacts the rearward end 3 of the tampon 2. This position, when the front end portion 22 of the pusher element 20 abuts against the rearward end 3 of the tampon 2, is illustrated in FIG. 2. In this position the applicator is ready for use, and can be introduced into the vagina. Thereafter the push lever 30 is further turned towards the outer surface of the outer cylinder 10 with the thumb of the user pressing onto the support surface 36 of the push lever 30. By further turning the push lever 30 the pusher element 20 is advanced into the interior of the outer cylinder 10, thereby advancing the tampon 2 and pushing it out of delivery opening 12, as shown in FIG. 3. When further pressing on the push lever, thereby further advancing the pusher element 20, the tampon 2 eventually is completely pushed out, and the applicator may be withdrawn.

In the position as illustrated in FIG. 2 and during the further movement through positions as indicated in FIG. 3, the elongated pusher element 20 does not extend along a straight line but undergoes a certain bending along its longitudinal axis. After inserting the pusher element 30 through the opening 14 and further advancing the pusher element, it finally contacts the inner wall of the outer cylinder 10 in an area opposite to the opening 14, whereupon the pusher element slightly bends during its progressing movement in the general direction of the longitudinal axis of the outer cylinder. Flexibility or capability of bending is easily achievable if the pusher element is, as the embodiment illustrated, formed by a simple rod, the diameter of which can be dimensioned to achieve the desired flexibility.

Due to the bending of the pusher element 20, its length should be slightly larger than the distance from the opening 14 to the delivery opening 12 of the outer cylinder so that the pusher element can completely extend over this distance and push the tampon 2 completely out of the delivery opening.

What is claimed is:

1. A tampon applicator, comprising
    a hollow outer cylinder having a delivery opening at a front end for expelling a tampon having an initial position wherein a forward end of the tampon is adjacent the delivery opening and a rearward end is opposite thereof, the outer cylinder having an opening through its cylinder wall, the opening being located, in the longitudinal direction of the cylinder, behind the rearward end of the tampon when the tampon is in initial position adjacent the delivery opening;
    an elongated pusher element adapted to be insertible in and slidable through the opening from the exterior into the interior of the outer cylinder in order to abut with a forward end portion thereof against the rearward end of the tampon, the pusher element being capable of bending along a longitudinal direction thereof;
    a push lever pivotally conntected to a rearward end portion of the elongated pusher element and pivotally connected to the outer cylinder in a position behind the opening such that by pivoting the push lever forward towards the outer cylinder the elongated pusher element is advanced through the opening to expel the tampon through the delivery opening.

2. The tampon applicator according to claim 1, wherein the outer cylinder, the elongated pusher element and the push lever are integrally formed.

3. The tampon applicator according to claim 2, wherein the pivotal connection between the push lever and the outer cylinder is formed by a zone of reduced material thickness.

4. The tampon applicator according to claim 2, wherein the pivotal connection between the push lever and the pusher element is formed by a zone of reduced material thickness.

5. The tampon applicator according to claim 2, wherein the outer cylinder, the elongated pusher element and the push lever are in the form of a single-piece moulded plastic member.

6. The tampon applicator according to claim 1, wherein the push lever is provided with a support surface adapted to allow the thumb of the user to abut against the support surface while pressing and pivoting the push lever against the outer cylinder.

7. The tampon applicator according to claim 6, wherein the support surface is provided with a non-planar profile for avoiding sliding movements of the thumb against the support surface.

8. The tampon applicator according to claim 1, wherein the push lever, the pusher element, and the outer cylinder each have a length, and the sum of the lengths of the push lever and the pusher element is essentially equal to the length of the outer cylinder.

9. The tampon applicator according to claim 8, wherein the ratio of the length of the push lever to the length of the pusher element is about 1:2.

10. The tampon applicator according to any preceeding claim, wherein the outer surface of the outer cylinder is provided with at least one circumferential ring adapted to avoid longitudinal movement of the applicator when it is gripped between two fingers.

11. The tampon applicator according to claim 1, wherein at least parts of the outer surface of the outer cylinder are provided with non-planar gripping profiles to facilitate a secure grip.

12. The tampon applicator according to claim 1, wherein the outer cylinder is, on the rearward end, provided with a cut-out in the form of a slot for receiving a string of the tampon loaded in the applicator.

13. A method of expelling a tampon from a tampon applicator comprising (1) a hollow cylinder having a delivery opening at a front end and containing a tampon having an initial position wherein a forward end of the tampon is adjacent the delivery opening and a rearward end is opposite thereof, the outer cylinder having an opening located behind the rearward end of the tampon when the tampon is in the initial position, (2) an elongated pusher element that is capable of bending along a longitudinal direction, and (3) a push lever pivotally connected to both a rearward end portion of the elongated pusher element and pivotally connected to the outer cylinder behind the opening, the method comprising the steps of:

a) introducing a forward end of the pusher element through the opening until it abuts the rearward end of the tampon;

b) positioning the delivery opening of the outer cylinder at a desired location; and c) pressing on the push lever to advance the pusher element, thereby expelling the tampon through the delivery opening.

* * * * *